United States Patent

Takahashi et al.

[11] Patent Number: 5,337,731
[45] Date of Patent: Aug. 16, 1994

[54] ENDOSCOPE STAND

[75] Inventors: Nagashige Takahashi; Hiromichi Shibuya, both of Tokyo, Japan

[73] Assignee: Asahi Kogaku Kogyo Kabushiki Kaisha, Tokyo, Japan

[21] Appl. No.: 926,701

[22] Filed: Aug. 10, 1992

[30] Foreign Application Priority Data

Aug. 20, 1991 [JP] Japan ................... 3-293967

[51] Int. Cl.⁵ ............................................. A61B 1/00
[52] U.S. Cl. ........................................ 128/4; 248/121; 312/209
[58] Field of Search .................. 312/209; 128/4; 248/121, 122; 269/329, 902, 909; 604/163, 171, 192

[56] References Cited

U.S. PATENT DOCUMENTS

| 3,211,446 | 10/1965 | Headrick | 269/902 X |
| 3,824,744 | 7/1974 | Petrant | 269/902 X |
| 4,496,123 | 1/1985 | Laramie | 248/121 |
| 4,572,594 | 2/1986 | Schwartz | 312/209 |
| 4,607,897 | 8/1986 | Schwartz | 312/209 |
| 4,620,527 | 11/1986 | Adams, Jr. | 128/4 |
| 4,730,880 | 3/1988 | Schmidt et al. | 312/209 |
| 4,907,395 | 3/1990 | Opie et al. | |
| 4,991,325 | 2/1991 | Teduschi | 248/121 X |
| 4,997,084 | 3/1991 | Opie et al. | |
| 5,013,299 | 5/1991 | Clark | 312/209 X |
| 5,059,271 | 10/1991 | Taub | 269/909 X |
| 5,064,154 | 11/1991 | Payne | 248/121 |

FOREIGN PATENT DOCUMENTS 2-57228  2/1990  Japan .

OTHER PUBLICATIONS

Fiberscope Cleaning and Disinfection; "Fiberscope Disinfection Cart: The Endoscopy Assistant's Third Hand"; 1986.

Primary Examiner—Richard J. Apley
Assistant Examiner—Karen A. Jalbert
Attorney, Agent, or Firm—Sandler, Greenblum & Bernstein

[57] ABSTRACT

An endoscope stand for supporting an endoscope having a control part where the proximal end portion of a light guide cable includes a light guide connector attached to the distal end thereof and the proximal end portion of an insert tube being connected to each other. The endoscope stand comprises a control part support member for supporting the control part of the endoscope substantially horizontally, an insert tube supporting member which is disposed substantially horizontally to place the insert tube of the endoscope thereon, cover sheets which are impermeable to water. The cover sheets are removably placed on the control part supporting member and the insert tube supporting member, respectively. A light guide connector supporting member supports the light guide connector so that the light guide cable will not touch any of the surroundings.

13 Claims, 7 Drawing Sheets

FIG. 12 bbbb# ENDOSCOPE STAND

BACKGROUND OF THE INVENTION

The present disclosure relates to subject matter contained in Japanese Patent application No. 3-293967 (filed on Aug. 20, 1991), which is expressly incorporated herein by reference in its entirety.

1. Field of the Invention

The present invention relates to a stand for supporting an endoscope when a sheath is fitted over and removed from an insert tube of the endoscope to prevent contagion of bacteria and viruses.

2. Description of the Prior Art

Conventional endoscope stands of the type described above include one which is designed to retain a control part of an endoscope in such a way that the insert tube of the endoscope is downwardly suspended, and another in which the whole endoscope is placed horizontally on a single supporting plate.

However, the conventional endoscope stand wherein the insert tube of the endoscope is downwardly suspended suffers from the problem that the insert tube is likely to sway and touch the surroundings, resulting in the insert tube being contaminated before actual use. When a used endoscope is supported on the stand, the endoscope may contaminate the surroundings.

The prior art wherein the whole endoscope is placed horizontally on a single supporting plate also has the problem of contamination occurring between the insert tube of the endoscope and the surface of the supporting plate in the same way as in the case of the above. Further, since it is difficult to wrap the control part of the endoscope with a cover and remove the cover therefrom with the endoscope laid on the supporting plate, contamination of the control part cannot be prevented. In addition, a light guide cable that is connected to a light source apparatus may also be contaminated because it is always in contact with the surface of the supporting plate.

SUMMARY OF THE INVENTION

An object of the present invention is to provide a stand for an endoscope which is designed so that a sheath can be fitted over and removed from the insert tube of the endoscope efficiently without contaminating the endoscope and the stand.

Other objects and advantages of the present invention will become apparent from the following detailed description of an illustrated embodiment of the invention.

According to the present invention, there is provided an endoscope stand for supporting an endoscope having a control part where the proximal end portion of a light guide cable having a light guide connector attached to the distal end thereof and the proximal end portion of an insert tube are connected to each other, comprising: a control part supporting member for supporting the control part of the endoscope substantially horizontally; an insert tube supporting member which is disposed substantially horizontally to place the insert tube of the endoscope thereon; cover sheets which are impermeable to water, the sheets being removably placed on the control part supporting member and the insert tube supporting member, respectively; and a light guide connector supporting member for supporting the light guide connector so that the light guide cable will not touch any of the surroundings.

BRIEF DESCRIPTION OF THE DRAWINGS

The present invention may be more fully understood from the description of preferred embodiments of the invention set forth below, together with the accompanying drawings, in which.

DESCRIPTION OF THE EMBODIMENT

One embodiment of the present invention will be described below with reference to the accompanying drawings.

Figure 1:
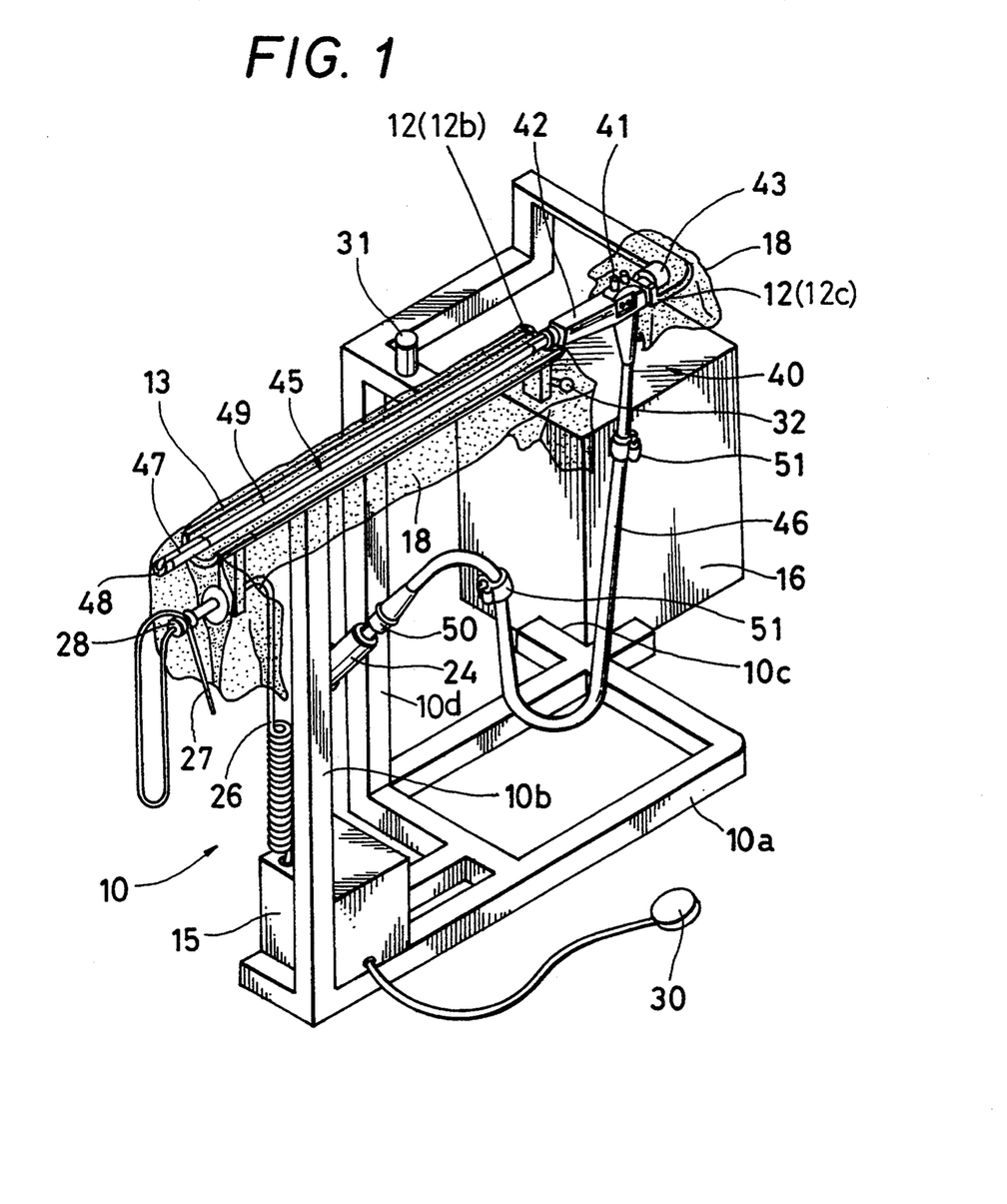
FIG. 1 is a perspective view showing the general arrangement of one embodiment of the present invention.

FIG. 1 shows an endoscope 40 which is supported on an endoscope stand 10.

The endoscope 40 has a control part 42 which incorporates an air-water supply and suction controller 41 and other elements. An eyepiece 43 is provided on the top of the control part 42, and an insert tube 45 and a light guide cable 46 are connected to the lower end and the rear side, respectively, of the control part 42.

The insert tube 45 is formed from a flexible tube over the entire length thereof. A bendable portion 47 is formed at the distal end of the insert tube 45 such that the bendable portion 47 is bendable by remote control from the control part 42, and a distal end block 48 is connected to the distal end of the bendable portion 47, the block 48 being provided with viewing and illuminating windows.

In addition, the insert tube 45 is formed with a groove 49 with a U-shaped cross-sectional configuration which extends over the entire length of the tube 45 so that a tube for air supply, water supply and suction can be passed through the groove 49 from the distal end of the insert tube 45 to the control part 42.

The light guide cable 46 is a flexible tube having an illuminating light guide fiber bundle extending therethrough. A light guide connector 50 which is to be connected to a light source apparatus is attached to the distal end of the light guide cable 46. Reference numeral 51 denotes tube securing members used to secure an air-water supply and suction tube 63 (described later in connection with FIG. 10) along the light guide cable 46.

The endoscope stand 10 comprises a base 10a, two support posts 10b and 10d which are set upright on the base 10a, a control part supporting plate 12 which comprises two separate plate portions 12b and 12c for supporting the control part 42 placed thereon, and an insert tube supporting plate 13 for supporting the insert tube 45 placed thereon.

The supporting plates 12 and 13 are formed on the two support posts 10b and 10d. More specifically, the insert tube supporting plate 13 is attached to the upper end of the first support post 10b. The first plate portion 12b of the control part supporting plate 12 is formed at one end of the insert tube supporting plate 13, and the second plate portion 12c of the control part supporting plate 12 is attached to the upper end of the second support post 10d at a distance from the first plate portion 12b.

In addition, an air pump 15 with an air pressure controller for inflating a sheath (described later) is provided on the base 10a, and a waste box 16 for accommodating a sheath to be discarded is disposed in contact with a right angle portion 10c formed on the base 10a.

Figure 2:
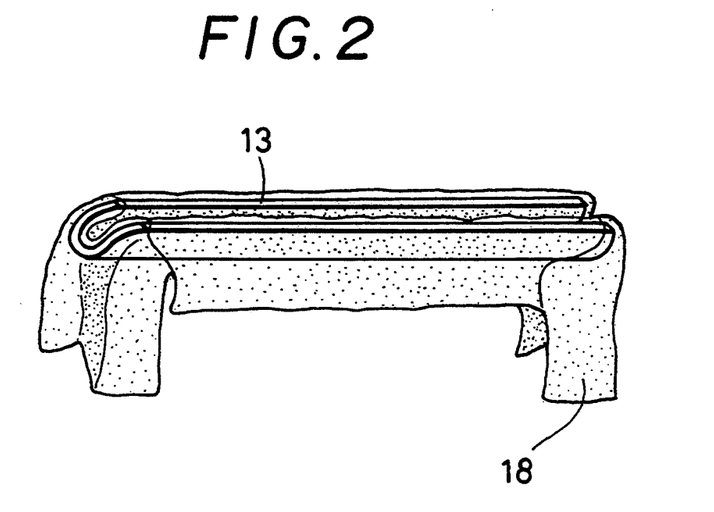
FIG. 2 is a perspective view showing an essential part of the embodiment of the present invention.
Figure 3:
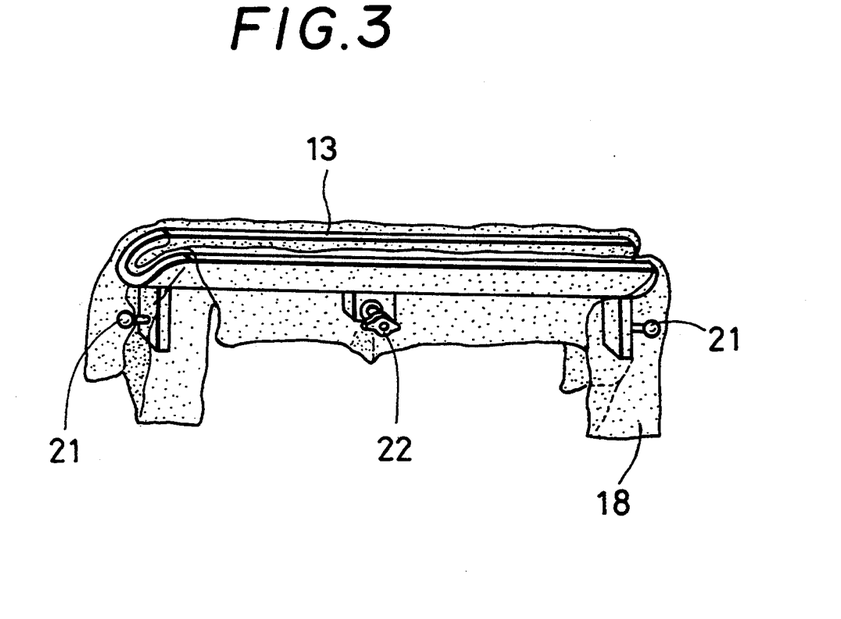
FIG. 3 is a perspective view showing an essential part of a modification of the embodiment of the present invention.

The control part supporting plate 12 and the insert tube supporting plate 13 are covered with respective cover sheets 18 which are impermeable to water, e.g., nonwoven fabric, as shown in FIG. 2. Since the cover sheets 18 cannot be stationarily set in position simply by putting them over the supporting plates 12 and 13, the cover sheets 18 are creased in conformity to the respective shapes of the supporting plates 12 and 13 so that the cover sheets 18 fit snugly to the supporting plates 12 and 13. It should be noted that the cover sheet 18 may be fixed by pins 21, an air supply port 22, etc., which are provided on the insert tube supporting plate 13, as shown in FIG. 3.

It should be noted that the elements which are present inside the cover sheets 18 are shown by the solid lines with a view to facilitating understanding.

The insert tube supporting plate 13 is formed in the shape of an elongate, straight gutter having a uniform semicircular cross-sectional configuration, and it is disposed horizontally, as shown in FIG. 2. However, the insert tube supporting plate 13 may have any cross-sectional configuration, e.g., a V- or U-shaped cross-sectional configuration, provided that the center of the cross-section of the supporting plate 13 is recessed so that the insert tube 45 can be stably placed thereon.

Figure 4:
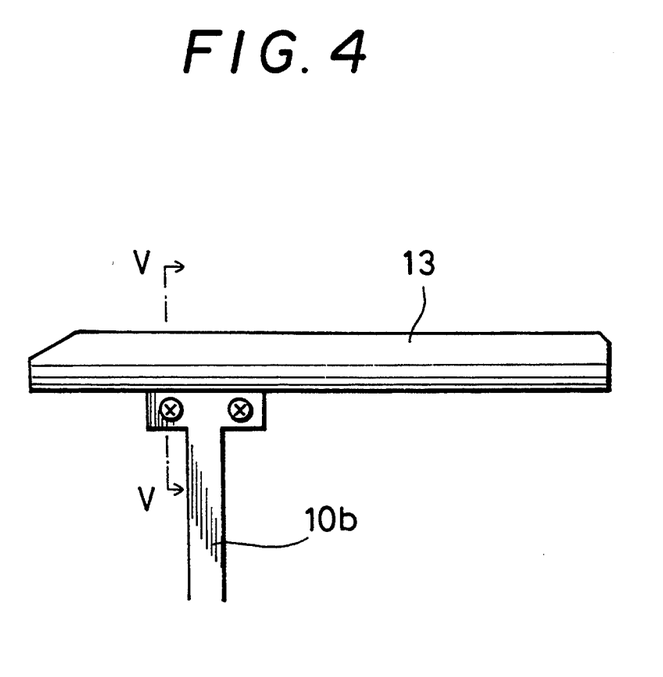
FIG. 4 is a side view showing an essential part of another modification of the embodiment of the present invention.
Figure 5:
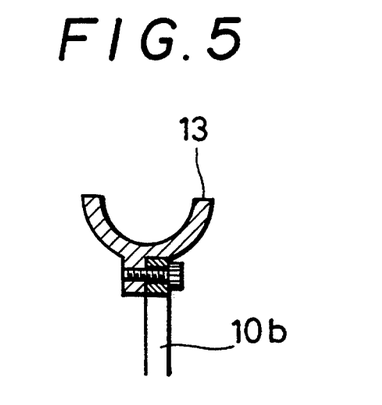
FIG. 5 is a sectional view taken along line V—V in FIG. 4.
Figure 6:
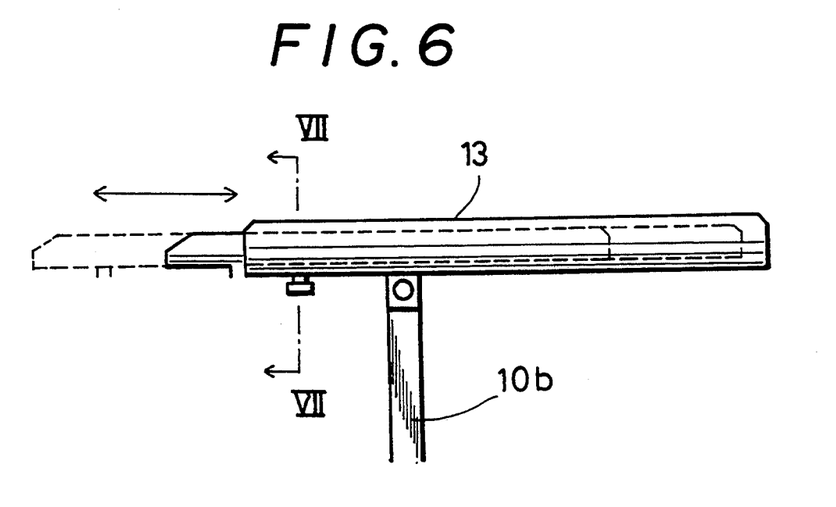
FIG. 6 is a side view showing an essential part of still another modification of the embodiment of the present invention.
Figure 7:
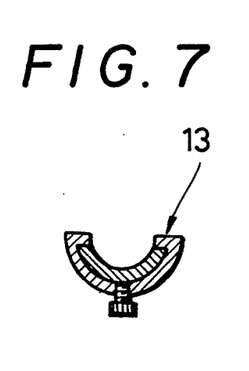
FIG. 7 is a sectional view taken along the line VII—VII in FIG. 6.

In addition, the insert tube supporting plate 13 may be detachably attached to the upper end of the support post 10b by using screws so that the insert tube supporting plate 13 can be replaced with another in conformity to the length of the insert tube 45 of the endoscope 40, as shown in FIGS. 4 and 5. Alternatively, the insert tube supporting plate 13 may be formed in a telescopic structure so that the length thereof is variable, as shown in FIGS. 6 and 7.

Figure 8:
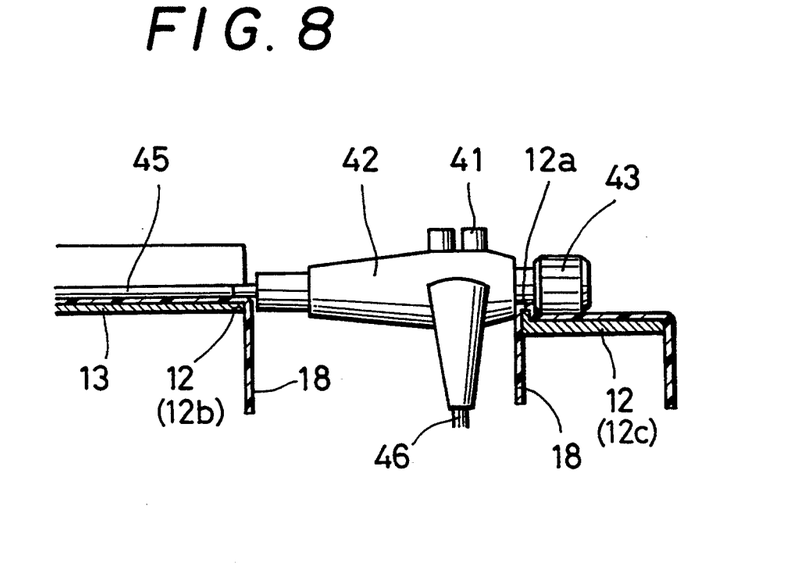
FIG. 8 is a partly-sectioned side view showing an essential part of the embodiment of the present invention.

Referring to FIG. 8, which shows the control part 42 which is placed on the control part supporting plate 12 (12b and 12c), the control part 42 is supported horizontally on the cover sheets 18 at both longitudinal ends thereof, that is, the joint portion of the control part 42 which is connected to the insert tube 45, and the eyepiece 43.

Thus, the two plate portions 12b and 12c constituting the control part supporting plate 12 are formed only at the respective positions corresponding to the longitudinal end portions of the control part 42 with a space provided therebetween. Accordingly, it is possible to wrap a control part cover (not shown) around the control part 42, unwrap it and disassemble a bending control knob (not shown) with ease by rotating the control part 42 as desired. It is also possible to prevent the light guide cable 46 from touching the control part supporting plate 12.

Figure 9:
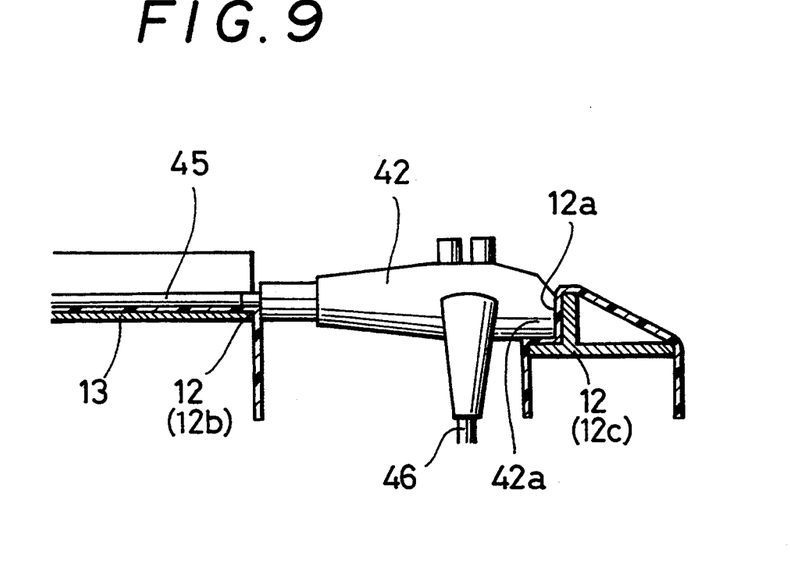
FIG. 9 is a partly-sectioned side view showing an essential part of a modification of the embodiment of the present invention.

In the case of a video endoscope having a solid-state imaging device incorporated in the distal end block 48, the upper end portion 42a of the control part 42 may be supported by the control part supporting plate 12, as shown in FIG. 9, because it has no eyepiece 43.

In either case, a stopper 12a is formed so that the control part 42 placed on the control part supporting plate 12 cannot move longitudinally (either rightwardly or leftwardly as viewed in the figures). Accordingly, even when a sheath is fitted over or removed from the insert tube 45 with the control part 42 supported on the control part supporting plate 12, the endoscope 40 is stably maintained in the stationary state on the stand 10.

It should be noted that the first plate portion 12b of the control part supporting plate 12 may be omitted as long as the control part 42 can be held in a stable condition by the fact that the insert tube 45 is supported by the insert tube supporting plate 13 even if the control part 42 is not supported by the end portion of the insert tube supporting plate 13 (i.e., the first plate portion 12b of the control part supporting plate 12).

Referring back to FIG. 1, reference numeral 24 denotes a connector socket for rotatably supporting the light guide connector 50 inserted therein. The connector socket 24 is formed from a cylindrical member that is provided to face obliquely upward on the intermediate part of the support post 10b. When the light guide connector 50 is inserted into the connector socket 24, the light guide cable 46 can be set so that it will not touch any of the surroundings, i.e., the base 10a, the support posts 10b and 10d, etc. At this time, the intermediate portion of the light guide cable 46 is suspended in a U-shape and hence unlikely to be twisted or twined. In addition, the air-water supply and suction tube 63 can be readily attached to and detached from the tube securing members 51.

An air supply tube 26 is connected at one end thereof to the air pump 15 and secured at the other end to the lower side of the forward end portion of the insert tube supporting plate 13. An air injection tube 27 is detachably connected to the end of the air supply tube 26 at the forward end portion of the supporting plate 13. Reference numeral 28 denotes a hook with which the distal end of the air injection tube 27 can be engaged, and 30 a foot switch for turning on-off the air pump 15 by foot.

A tube hook pin 31 is used to hook the air-water supply and suction tube 63 in a coiled up condition. A sheath bag securing pin 32 is used to secure the mouth portion 70a of a sheath bag 70 (described later). These pins 31 and 32 will be described below with reference to FIGS. 10 to 12.

Figure 10:
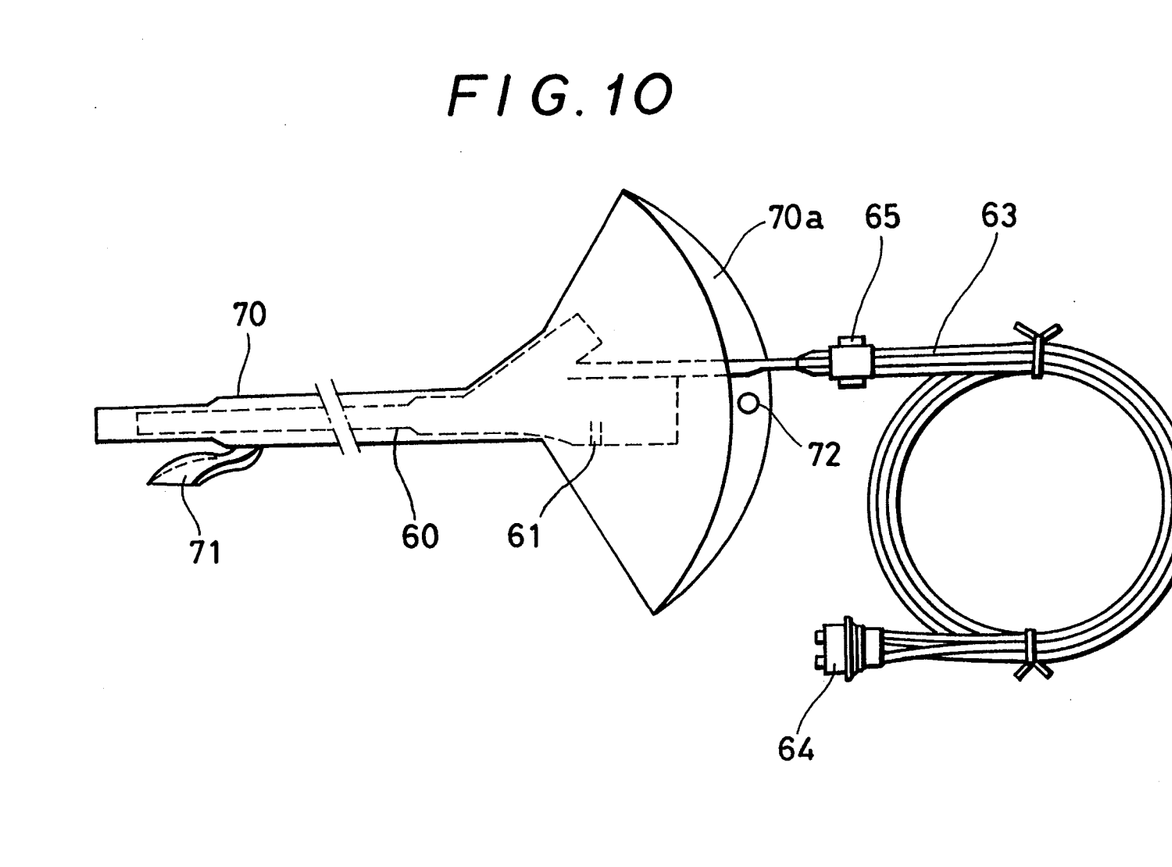
FIG. 10 is a plan view showing a sheath and a sheath bag in the embodiment of the present invention.

FIG. 10 shows a sheath 60 that is removably fitted over the insert tube 45 of the endoscope 40 and a sheath bag 70 for wrapping the sheath 60 when fitted over and removed from the insert tube 45.

The sheath 60 and the sheath bag 70 are two discrete members, which are completely independent of each other, so that the sheath 60 can be inserted into and removed from the sheath bag 70 through the mouth portion 70a of the sheath bag 70.

The sheath 60 can be inflated by sending air to the inside thereof from an air supply port 61 when sheath 60 is to be fitted over and removed from the insert tube 45 of the endoscope 40. The sheath bag 70 prevents excessive inflation of the sheath 60.

The air-water supply and suction tube 63 communicates with an air-water supply and suction port (not shown) that opens at the distal end of the sheath 60. The tube 63 passes through the sheath 60 and extends from the proximal end of the sheath 60.

Further, a connector 64 for connection with air supply, water supply and suction mouthpieces, which are provided on the light source apparatus (not shown), is attached to the proximal end of the air-water supply and suction tube 63. In addition, an intermediate connector 65, which is connected to the air-water supply and suction controller 41 in the control part 42, is attached to the intermediate portion of the tube 63.

In a preparatory stage before actual use, the air-water supply and suction tube 63 is held in a coiled-up state. During an operation immediately before the tube 63 is attached to the endoscope 40, the tube 63 can be hooked in the coiled-up state on the tube hook pin 31 provided on the stand 10.

Figure 11:
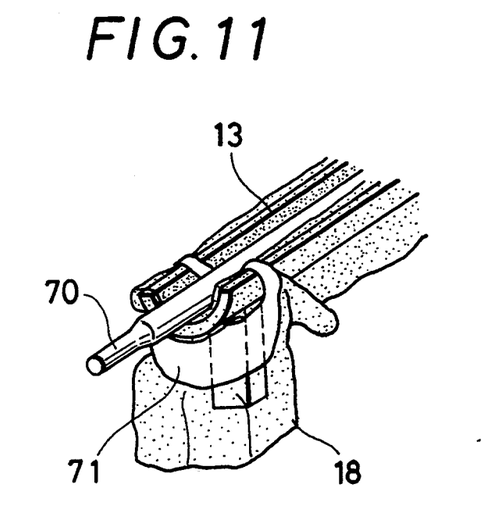
FIG. 11 is a fragmentary perspective view of the embodiment having the sheath bag attached thereto.

A ring 71 is formed on the distal end portion of the sheath bag 70 so as to wrap around the distal end portion of the insert tube supporting plate 13 of the stand 10, thereby securing the sheath bag 70 thereto. FIG. 11 shows a method in which the distal end of the sheath bag 70 is secured to the insert tube supporting plate 13.

Figure 12:
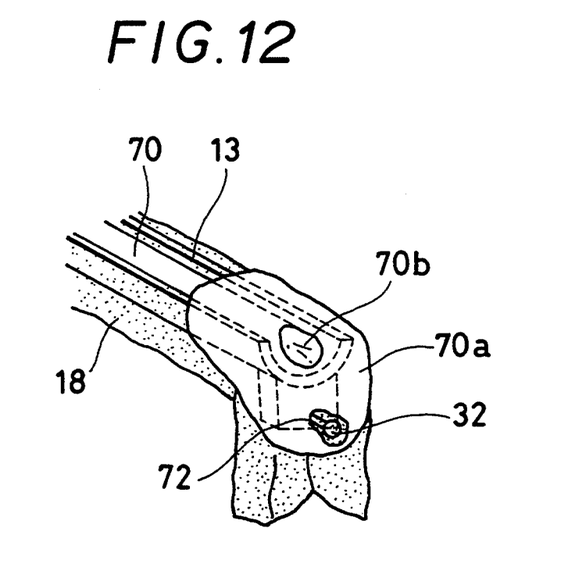
FIG. 12 is a fragmentary perspective view of the embodiment having the sheath bag attached thereto.

In the meantime, the mouth portion 70a of the sheath bag 70 opens in the shape of a large bell, and an engagement hole 72 is formed in the end portion of the mouth portion 70a to engage with the sheath bag securing pin 32. FIG. 12 shows a method in which the engagement hole 72 is engaged with the sheath bag securing pin 32. The mouth portion 70a is turned up to a substantial degree, so that the inlet 70b of the sheath bag 70 is exposed.

Thus, the sheath bag 70 can be secured at both the forward and rearward ends thereof to the insert tube supporting plate 13. However, it should be noted that the sheath bag securing structure is not necessarily limited to the above and that other securing structures may be employed.

The method of using the endoscope stand 10 of the above-described embodiment will be explained below.

To use the endoscope 40, first, clean cover sheets 18 are put over the insert tube supporting plate 13 and the control part supporting plate 12, respectively, and the insert tube 45 and control part 42 of the endoscope 40 are placed on the respective cover sheets 18. At this time, even if either the endoscope 40 or the endoscope stand 10 has been contaminated, the clean one will not be contaminated because the endoscope 40 and endoscope stand 10 are isolated from each other by the cover sheets 18.

Next, the light guide connector 50 is inserted into the connector socket 24. Thus, setting of the endoscope 40 to the endoscope stand 10 is completed.

Subsequently, the distal end of the air injection tube 27 is inserted into the air supply port 61 of the sheath 60, and the foot switch 30 is stepped on, thereby inflating the sheath 60 inside the sheath bag 70. When the outer diameter of the sheath 60 reaches the inner diameter of the sheath bag 70, the sheath 60 does not inflate any longer, so that excess air is released into the atmosphere by the operation of a relief valve (not shown).

In this state (shown in FIG. 10), the sheath 60, together with the sheath bag 70, is fitted over the insert tube 45 of the endoscope 40 from the distal end of the latter.

After the sheath 60 has been fitted over the insert tube 45 as far as the proximal end thereof, the air injection tube 27 is detached from the sheath 60, and a control part cover (not shown) is wrapped around the control part 42 of the endoscope 40.

Further, the air-water supply and suction tube 63 is secured to the tube securing members 51 attached to the light guide cable 46 so that the tube 63 extends along the light guide cable 46, and the intermediate connector 65 is connected to the air-water supply and suction controller 41.

Subsequently, the sheath bag 70 is secured to the insert tube supporting plate 13, as described in connection with FIGS. 11 and 12, and then the control part 42 is moved so that the insert tube 45 covered with the sheath 60 is drawn out from the sheath bag 70.

Finally, the light guide connector 50 and the connector 64 are each connected to a predetermined portion of the light source apparatus (not shown). Thus, the control part 42 and insert tube 45 of the endoscope 40 can be used for a clinical inspection in a state where the control part 42 and the insert tube 45 are covered with the control part cover and the sheath 60, respectively.

Upon completion of the use of the endoscope 40, the light guide connector 50 and the connector 64 are first detached from the light source apparatus, and then the light guide connector 50 is inserted into the connector socket 24 of the endoscope stand 10.

Then, the doctor (user) holds the control part 42 in one hand and the insert tube 45 in the other, and in this state, he or she inserts the insert tube 45 into the sheath bag 70, which is attached to the insert tube supporting plate 13 of the endoscope stand 10.

Subsequently, the air-water supply and suction tube 63 and the intermediate connector 65 are detached from the tube securing members 51, which are attached to the light guide cable 46 and the control part 42, respectively, and the air-water supply and suction tube 63, including the connector 64 and the intermediate connector 65, is disconnected from the sheath 60 and discarded into the waste box 16.

Next, the control part cover is removed from the control part 42, and the sheath 60 is inflated again inside the sheath bag 70 and then removed from the insert tube 45, together with the sheath bag 70. The control part cover, the sheath 60 and the sheath cover 70 are all discarded into the waste box 16. At this time, the air injection tube 27 is disconnected from the stand 10 and then discarded or disinfected for reuse.

Thus, elements that have touched the patient's body or mucus, blood, etc. coming out of the patient's body cavity during the clinical inspection are all discarded into the waste box 16, and at this time the endoscope 40 and the endoscope stand 10 are not contaminated at all.

According to the present invention, it is possible to efficiently perform the operation of fitting a sheath over the insert tube of the endoscope and removing the former from the latter and the operation of putting a cover on the control part of the endoscope and removing the former from the latter without contaminating the endoscope and the endoscope stand and without the need for an assistant to the doctor (user).

While the invention has been described by reference to a specific embodiment chosen for purposes of illustration, it should be apparent that numerous modifications could be made thereto by those skilled in the art without departing from the basic concept and scope of the invention.

We claim:

1. An endoscope stand for supporting an endoscope having a control part, and wherein a proximal end portion of a light guide cable having a light guide connector being attached to a distal end thereof, and a proximal end portion of a flexible insert tube being connected to each other, said flexible insert tube having a length, said endoscope stand comprising:
   a control part supporting member for supporting said control part of said endoscope substantially horizontally;
   an insert tube supporting member which is disposed substantially horizontally to place said flexible insert tube of said endoscope thereon, said insert tube supporting member having means for supporting said flexible insert tube at spaced points over substantially the length thereof;
   cover sheets which are impermeable to water, said cover sheets being removably placed on said control part supporting member and said insert tube supporting member, respectively when said control part supporting member supports said control part and said insert tube supporting member supports said flexible insert tube, said insert tube supporting member including a member for securing said cover sheets; and
   a light guide connector supporting member for supporting said light guide connector so that said light guide cable will not touch any of the surroundings.

2. An endoscope stand according to claim 1, wherein said control part supporting member and said insert tube supporting member are provided on support posts which are set upright.

3. An endoscope stand according to claim 1, wherein said control part supporting member comprises two separate supporting portions formed only at positions corresponding to the two end portions of said control part of said endoscope with a space provided therebetween.

4. An endoscope stand according to claim 3, wherein one of said two portions of said control part supporting member is formed at one end of said insert tube supporting member.

5. An endoscope stand according to claim 1, wherein said control part supporting member is provided with a stopper for limiting longitudinal movement of said control part of said endoscope.

6. An endoscope stand according to claim 1, wherein said insert tube supporting member is formed with a cross-section, the center of which is recessed for placement of said insert tube of said endoscope.

7. An endoscope stand according to claim 1, wherein said insert tube supporting member is replaceable.

8. An endoscope stand according to claim 1, wherein said insert tube supporting member is telescopic so that the length thereof is variable.

9. An endoscope stand according to claim 1, wherein said cover sheets are creased in conformity to the respective shapes of said control part supporting member and said insert tube supporting member.

10. An endoscope stand according to claim 1, wherein said light guide connector supporting member is a cylindrical member which is positioned to face obliquely upward so as to support said light guide connector inserted therein.

11. An endoscope stand according to claim 1, further comprising air supply means for inflating a sheath which is removably fitted over said insert tube of said endoscope.

12. An endoscope stand according to claim 1, further comprising a member for hooking a sheath bag for wrapping a sheath which is removably fitted over said insert tube of said endoscope.

13. An endoscope stand according to claim 1, further comprising a waste box for accommodating waste.

* * * * *